United States Patent [19]
Ralston

[11] Patent Number: 5,888,756
[45] Date of Patent: Mar. 30, 1999

[54] DIAGNOSING A PREDISPOSITION FOR EQUINE OSTEOCHONDRITIS DISSECANS

[75] Inventor: Sarah L. Ralston, Jackson, N.J.

[73] Assignee: Rutgers, The State University of New Jersey, New Brunswick, N.J.

[21] Appl. No.: 899,980

[22] Filed: Jul. 24, 1997

Related U.S. Application Data

[60] Provisional application No. 60/023,273, Jul. 24, 1996.

[51] Int. Cl.$^6$ .............................. C12Q 1/54; C12Q 1/00; G01N 33/53
[52] U.S. Cl. ............................... 435/14; 435/4; 435/283; 435/975; 435/968; 435/970
[58] Field of Search ................................. 435/14, 4, 283, 435/975, 968, 970

[56] References Cited

U.S. PATENT DOCUMENTS

| | | | |
|---|---|---|---|
| 5,077,296 | 12/1991 | Drizen et al. ........................... | 514/261 |
| 5,374,533 | 12/1994 | Matsuzawa et al. ..................... | 435/14 |

OTHER PUBLICATIONS

Anderson et al., "Nutrition in health and disease," 17th Ed. J.B. Lippincott Company, Philadelphia, PA, pp. 88–90 (1992).
Garcia et al., "Equine intravenous glucose tolerance test: Glucose and insulin responses of healthy horses fed grain or hay and of horses with pituitary adenoma," Am. J. Res, 47:570–572 (Mar., 1986).
Gaustad et al., "Lameness in three–year–old Standardbred trotters—influence of parameters determined during the first year of life," J. Eq. Vet. Sci., 15:233–239 (1995).
Glade et al., "A Dietary Etiology for Osteochondrotic Cartilage," Equine Veterinary Science, 6:151–154.
Glade, "The control of cartilage growth in osteochondrosis: a review," J. Eq. Vet. Sci., 6:175–187 (1986).
Grondahl et al., "Heritability estimations of osteochondrosis in the tibiotarsal joint and bony . . . ," J. Am. Vet. Med. Assoc., 203:101–104 (1993).
Grondahl, "The incidence of osteochondrosis in the tibiotarsal joint of Norwegian Standardbred trotters," Eq. Vet. Sci., 11:272, (1991).
Hoppe, "Radiological investigations of osteochondrosis dissecans in Standardbred trotters and Swedish Warmblood horses," Eq. Vet. J., 16:425–429 (1984).
Jeffcott et al., "Nutrition and Developmental Orthopedic Disease," Nutrition, 11:299 (Nov., 1990).
Jeffcott, "Osteochondrosis in the horse—searching for the key to pathogenesis," Eq. Vet. J., 23:331–338 (1991).
Krook et al., "Fractures in Thoroughbred racehorses," Cornell Vet., 78 (Suppl.) 11:5–133 (1988).
Laws et al., "Racing performance of Standardbreds after conservative and surgical treatment for tarsocrural osteochondrosis," Equine Vet. J. 25:199–202 (1993).
Lewis, "Equine Clinical Nutrition," Williams and Wilkins, Philadelphia, PA, pp. 50–51, 429–433 (1995).
Malinowski et al., "Acute effects of short term starvation and refeeding on circulating concentrations of thyroid hormones . . . ", J. of Animal Science 73:184, 1995, (abstract).
McIllwraith et al.,"Osteochondritis dissecans of the tarsocroral joint: results of treatment with arthroscopic surgery," Eq. Vet. J., 23:155–162 (1991).

(List continued on next page.)

*Primary Examiner*—Louise N. Leary
*Attorney, Agent, or Firm*—Fish & Richardson, P.C.

[57] ABSTRACT

A method of predicting in a subject horse the presence or absence of a predisposition for osteochondritis dissecans, including performing a glucose tolerance test on the subject horse, and comparing the glucose tolerance test results of the subject horse and the glucose tolerance test results of an osteochondritis dissecans-free horse population.

20 Claims, 3 Drawing Sheets

---

METHOD OF PREDICTING IN A HORSE THE PRESENCE OR ABSENCE OF A PREDISPOSITION FOR OSTEOCHONDRITIS DISSECANS

| I. | Perform a Glucose Tolerance Test on a Subject Horse as follows: |
|---|---|
| A. | collect baseline urine and/or blood samples; |
| B. | administer a glucose challenge to the subject horse; |
| C. | collect urine and/or blood samples at fixed time periods from the subject horse; and |
| D. | measure glucose and/or insulin concentrations in the urine and/or blood samples. |

| II. | Compare the following Glucose Tolerance Test Results of the Subject Horse and of an Osteochondritis Dissecans-Free Horse Population: |
|---|---|
| A. | postprandial increases in urine and/or blood glucose concentrations; |
| B. | postprandial increases in blood insulin concentrations; |
| C. | the rate of postprandial increases in urine and/or blood glucose concentrations; and/or |
| D. | the rate of postprandial increases in blood insulin concentrations. |

| III. | Diagnose the Subject Horse as Predisposed to Osteochondritis Dissecans where: |
|---|---|
| A. | the glucose tolerance test results of the subject horse exceed the numerical range of the test results of the osteochondritis dissecans-free horse population; |
| B. | the glucose tolerance test results of the subject horse exceed about two standard deviations or more above the mean test results of the osteochondritis dissecans-free horse population; or |
| C. | the glucose tolerance test results of the subject horse exceed about two standard deviations or more above the mean test results of the osteochondritis dissecans-free horse population. |

OTHER PUBLICATIONS

McIllwraith, "What is developmental orthopedic disease, osteochondrosis, ostechondritis, metabolic bone disease?", Proc. 39th Am. Assoc. Eq. Practitioners, pp. 35–44 (1993).

Philipsson et al., "Osteochondrosis in the tarsocrural joint and osteochondral fragments in the fetlock joints . . . ," Eqine Vet. J., Suppl. 16:38–41 (1993).

Ralston, "Comparison of digestion and growth in yearlings fed high versus low grain rations," J. Animal Sci., 72, Suppl. 1:262 (1994).

Ralston et al., "Plasma glucose and insulin concentrations and feeding behavior in ponies," J. Animal Sci., 54:1132–1137 (1982).

Ralston, "Hyperglycemia/hyperinsulinemia after feeding a meal of grain to young horses with osteochondritis dissecans (OCD) lesions".

Ralston, "The Effect of Diet on Acid–Base Status and Mineral Excretion in Horses," Equine Practice, 16:10–13 (1994).

Ralston, "Postprandial hyperglycemia/hyperinsulinemia in young horses with osteochondritis dissecans lesions," J. of Animal Science 73:184, 1995, (abstract).

Savage et al., "Effects of dietary energy and protein on induction of dyschondroplasia in foals," Osteochondrosis, 16:74–79 (1993).

Schougaard et al., "A radiographic survey of tibiotarsal osteochondrosis in a selected population of trotting horses in Denmark and its possible genetic significance," Eq. Vet. J., 22:288–289 (1990).

Wall, "Dietary cation–anion balance," Eq. Vet. Data, 12:17 (1991).

Watrous et al., "Osteochondrosis and juvenile spavin in equids," Am. J. Vet. Res, 52:607–612 (Apr., 1991).

Williams et al., "Developmental Orthopedic Disease: Minimizing the Incidence of a Poorly Understood Disorder," The Equine Athlete, 15:859–872 (Jun., 1993).

Williams et al; "The Equine Athlete"; V. 15 (6), pp. 859–872, 1993.

Garcia et al; "Am J. Vet. Res"; V47(3); pp. 570–572, 1986.

METHOD OF PREDICTING IN A HORSE THE PRESENCE OR ABSENCE OF A PREDISPOSITION FOR OSTEOCHONDRITIS DISSECANS

I. Perform a Glucose Tolerance Test on a Subject Horse as follows:

A. collect baseline urine and/or blood samples;

B. administer a glucose challenge to the subject horse;

C. collect urine and/or blood samples at fixed time periods from the subject horse; and D. measure glucose and/or insulin concentrations in the urine and/or blood samples.

II. Compare the following Glucose Tolerance Test Results of the Subject Horse and of an Osteochondritis Dissecans-Free Horse Population:

A. postprandial increases in urine and/or blood glucose concentrations;

B. postprandial increases in blood insulin concentrations;

C. the rate of postprandial increases in urine and/or blood glucose concentrations; and/or D. the rate of postprandial increases in blood insulin concentrations.

III. Diagnose the Subject Horse as Predisposed to Osteochondritis Dissecans where:

A. the glucose tolerance test results of the subject horse exceed the numerical range of the test results of the osteochondritis dissecans-free horse population;

B. the glucose tolerance test results of the subject horse exceed about two standard deviations or more above the mean test results of the osteochondritis dissecans-free horse population; or C. the glucose tolerance test results of the subject horse exceed about two standard deviations or more above the mean test results of the osteochondritis dissecans-free horse population.

FIG. 1

**METHOD OF SCREENING A POPULATION OF HORSES
FOR THE PRESENCE OR ABSENCE OF A
PREDISPOSITION TOWARD DEVELOPING OSTEOCHONDRITIS DISSECANS**

I. Perform a Glucose Tolerance Test on a Population of Horses as follows:

A. collect baseline urine and/or blood samples;

B. administer a glucose challenge to the population of horses;

C. collect urine and/or blood samples at fixed time periods from the population of horses; and     D. measure glucose and/or insulin concentrations in the urine and/or blood samples.

II. Calculate the Following Glucose Test Results for the Population of Horses:

A. postprandial increases in urine and/or blood glucose concentrations;

B. postprandial increases in blood insulin concentrations;

C. the rate of postprandial increases in urine and/or blood glucose concentrations; and/or     D. the rate of postprandial increases in blood insulin concentrations.

III. Diagnose a Horse having a Predisposition Toward Developing Osteochondritis Dissecans by Identifying a Horse having Glucose Tolerance Test Results which are Statistically Significantly Greater ($p < 0.05$) than the Mean Glucose Test Results of the Population of Horses with a Linear Regression Outlier Analysis

DIAGNOSING A PREDISPOSITION FOR EQUINE OSTEOCHONDRITIS DISSECANS

RELATED APPLICATIONS

This application relates to provisional application Ser. No. 60/023,273, filed Jul. 24, 1996.

This invention relates to animal diagnostics, and in particular, to methods, kits, computer systems, computer programs, and data sources for diagnosis, and more particularly to diagnosing a predisposition for equine osteochondritis dissecans.

BACKGROUND

Osteochondritis dissecans, or OCD, is the most clinically important manifestation of osteochondrosis, and is a major problem in the equine industry. Grondahl, A. M., The incidence of osteochondrosis in the tibiotarsal joint of Norwegian Standardbred trotters; Eq. Vet. Sci. 11:273–274 (1991); and Jeffcott, L. B., Osteochondrosis in the horse—searching for the key to pathogenesis, Eq. Vet. J. 23:331–338 (1991). Radiographic evidence of osteochondrotic lesions reduces the perceived potential for optimal performance, and therefore, the value of young horses. Gaustad G., et al., Lameness in three-year-old Standardbred trotters—influence of parameters determined during the first year of life; J. Eq. Vet. Sci. 15:233–239 (1995); Laws, E. G., et al., Racing performance of Standardbreds after conservative and surgical treatment for tarsocrural osteochondrosis; Eq. Vet. J. 25:199–202 (1993); and McIllwraith, C. W., et al., Osteochondritis dissecans of the tarsocrural joint: results of treatment with arthroscopic surgery; Eq. Vet. J. 23:155–162 (1991); and McIllwraith, C. W., What is developmental orthopedic disease, osteochondrosis, osteochondritis, metabolic bone disease?; Proc. 39th Am. Assoc. Eq. Practitioners, pp. 35–44 (1993). Osteochondritis dissecans has been identified as a contributing factor in catastrophic breakdowns in racehorses, which are detrimental to public perception and acceptance of racing sports. Krook, K., et al., Fractures in Thoroughbred racehorses; Cornell Vet. 78, (Suppl.) 11:5–133 (1988).

Osteochondritis dissecans is very common in Standardbred horses and primarily affects the hock. Hoppe, F., Radiological investigations of osteochondrosis dissecans in Standardbred trotters and Swedish Warmblood horses; Eq. Vet. J. 16:425–429 (1984); and McIllwraith, C. W., et al., Osteochondritis dissecans of the tarsocrural joint: results of treatment with arthroscopic surgery; Eq. Vet. J. 23:155–162 (1991). Lesions usually develop in horses between three to twelve months of age, with new lesions rarely appearing in horses over a year old, although clinical signs of lameness may not appear until the horse is put into work. Jeffcott, L. B., Osteochondrosis in the horse—searching for the key to pathogenesis; Eq. Vet. J. 23:331–338 (1991). Multiple causes have been proposed for osteochondritis dissecans, including genetics, trauma, endocrine/metabolism, and nutrition. Williams, M. A., et al., Developmental orthopedic disease: minimizing the incidence of a poorly understood disorder; The Compendium 15:859–872 (1993).

A genetic predisposition to osteochondritis dissecans has been well documented in the Standardbred horse. Gaustad G., et al., Lameness in three-year-old Standardbred trotters—influence of parameters determined during the first year of life; J. Eq. Vet. Sci. 15:233–239 (1995); and Schougaard, et al., A radiological survey of tibiotarsal osteochondrosis in a selected population of trotting horses in Denmark and its possible genetic significance; Eq. Vet. J. 22:288–289 (1990); Grondahl, et al., Heritability estimations of osteochondrosis in the tibiotarsal joint and bony fragments in the palmar/plantar portion of the metacarpo- and metatarsophalangeal joints of horses; J. Am. Vet. Med. Assoc. 203:101–104 (1993); and Philipson, J., et al., Osteochondrosis in the tarsocrural joint and osteochondral fragments in the fetlock joints in Standardbred Trotters II: Heritability; Eq. Vet. J. (Suppl.) 16:38–41 (1993). However, because the nature of the hereditary defect which increases the risk of osteochondritis dissecans in horses has not been identified, a suitable genetic screen is unavailable.

Another proposed factor in the development of osteochondritis dissecans is the type of ration fed to young (<1 year old) horses. Jeffcott, L. B., Osteochondrosis in the horse—searching for the key to pathogenesis; Eq. Vet. J. 23:331–338 (1991). For example, high grain rations are thought to be a potential cause of osteochondritis dissecans. However, not all young horses fed large amounts of grain develop osteochondritis dissecans. Glade, M. J., et al., A dietary etiology for osteochondrotic cartilage; J. Eq. Vet. Sci. 6:151–155 (1986); and Lewis, L. D., Equine Clinical Nutrition; Williams and Wilkins, Philadelphia, Pa., pp. 50–51, 429–433 (1995).

Ingestion of grain concentrate results in significant elevations in blood glucose and insulin concentration. Ralston, S. L., et al., Plasma glucose and insulin concentrations and feeding behavior in ponies; J. Animal Sci. 54:1132–1137 (1982). It has been postulated that such elevations in plasma insulin concentration may alter cartilage growth by influencing growth hormone and somatomedin release. Glade, M. J., The control of cartilage growth in osteochondrosis: a review; J. Eq. Vet. Sci. 65:175–187 (1986). It also has been hypothesized that osteochondritis dissecans may be associated with postprandial hyperglycemia and hyperinsulinemia and the resultant changes in thyroxine and growth hormone release. However, a definitive link between glucose intolerance and osteochondritis dissecans development has not previously been established. Glade, M. J., The control of cartilage growth in osteochondrosis: a review; J. Eq. Vet. Sci. 6:175–187 (1986); Glade, M. J., et al., A dietary etiology for osteochondrotic cartilage; Eq. Vet. Sci. 6:151–155 (1986).

Postprandial acidemia also may be influenced by insulin release. Glade, M. J., et al., A dietary etiology for osteochondrotic cartilage; Eq. Vet. Sci. 6:151–155 (1986). Postprandial acidemia is associated with enhanced urinary excretion of calcium, and possibly results from increased rates of bone resorption. Ralston, S. L., Dietary carbohydrates, acid base status and urinary calcium and phosphorus excretion in horses; Proc. 13th Equine Nutrition and Physiology Symposium, Gainesville, Fla., p. 42 (1993); and Wall, D. L., Dietary cation-anion balance, Eq. Vet. Data 12:17 (1991). Ingestion of grain concentrates by yearling horses reduces ($p<0.01$) venous pH (i.e., venous base excess and bicarbonate concentrations) in proportion to the amount ingested. Ralston, S. L., Comparison of digestion and growth in yearlings fed high versus low grain rations; J. Animal Sci. 72, Suppl. 1:262 (1994). Moreover, both an excess and a deficiency of zinc have been associated with the development of osteochondritis dissecans in young horses. Lewis, L. D., Equine Clinical Nutrition, Williams and Wilkins, Philadelphia, Pa., pp. 50–51, 429–433 (1995). Zinc can potentiate the synthesis and hypoglycemic action of insulin. Anderson, L., et al., Nutrition in health and disease, 17th Ed. J. B. Lippincott Company, Philadelphia, Pa., pp. 88–90 (1992).

Thus, numerous studies have investigated the possible causes of osteochondritis dissecans with a number of hypotheses resulting. In spite of this research and the deleterious impact of the disease on horses and horse racing, a test for diagnosing a predisposition for equine osteochondritis dissecans has not previously been developed.

SUMMARY

In general, in one aspect, the invention features a method of predicting in a subject horse the presence or absence of a predisposition for osteochondritis dissecans, including: performing a glucose tolerance test on the subject horse; and comparing the glucose tolerance test results of the subject horse and the glucose tolerance test results of an osteochondritis dissecans-free horse population, wherein glucose tolerance test results of the subject horse exceeding the numerical range of the glucose tolerance test results of the osteochondritis dissecans-free horse population are diagnostic of a predisposition for osteochondritis dissecans in the subject horse.

Implementations of the invention include one or more of the following features. The method, includes: a subject horse and horses in the osteochondritis dissecans-free population that are less than about sixteen months of age; the glucose tolerance test results include postprandial increases in blood glucose concentrations; the glucose tolerance test results include postprandial increases in blood insulin concentrations; the glucose tolerance test results include postprandial increases in blood glucose concentrations and blood insulin concentrations; the glucose test results include the rate of postprandial increases in blood glucose concentrations; the glucose tolerance test results include the rate of postprandial increases in blood insulin concentrations; and the glucose tolerance test results include the rate of postprandial increases in blood glucose concentrations and blood insulin concentrations.

In general, in one aspect, the invention features a method of predicting in a subject horse the presence or absence of a predisposition for osteochondritis dissecans, including: performing a glucose tolerance test on the subject horse; and comparing the glucose tolerance test results of the subject horse against the glucose tolerance test results of an osteochondritis dissecans-free horse population, wherein glucose tolerance test results of the subject horse exceeding about two standard deviations or more above the mean glucose tolerance test results of the osteochondritis dissecans-free horse population are diagnostic of a predisposition for osteochondritis dissecans in the subject horse.

In general, in one aspect, the invention features a method of screening a population of horses for the presence or absence of a predisposition toward developing osteochondritis dissecans, including: performing a glucose tolerance test on the population of horses; and identifying horses having glucose tolerance test results which are statistically significantly greater ($p<0.05$) than the mean glucose tolerance test results of the population by a linear regression outlier analysis, wherein the horses so identified are diagnosed as having a predisposition toward developing osteochondritis dissecans.

In general, in one aspect, the invention features a kit for predicting in a subject horse the presence or absence of a predisposition for osteochondritis dissecans, including: a field-administrable glucose challenge; a glucose concentration analysis system; and a data source containing glucose tolerance test results for an osteochondritis dissecans-free horse population.

Implementations of the invention include one or more of the following features. The kit, includes: a standardized concentrate for oral administration; a calorimetric glucose indicator strip; a blood glucose indicator strip; an electronic glucose analyzer; an electronic blood glucose analyzer; the data source is stored in the electronic glucose analyzer; the electronic glucose analyzer compares the postprandial increase in glucose concentration of a subject horse to the glucose tolerance test results of the osteochondritis dissecans-free horse population to render a diagnosis of a predisposition for osteochondritis dissecans; and a venous blood collection and containment system for laboratory analysis of blood glucose and insulin concentrations.

In general, in one aspect, the invention features a kit for predicting in a subject horse the presence or absence of a predisposition for osteochondritis dissecans, including: a field-administrable glucose challenge; a venous blood collection and containment system; instructions for performing a field glucose tolerance test; and a data source containing glucose tolerance test results of an osteochondritis dissecans-free horse population for comparison to glucose tolerance test results in a subject horse and diagnosing the presence or absence of a predisposition for osteochondritis dissecans in the subject horse.

In general, in one aspect, the invention features a computer system for predicting in a subject horse the presence or absence of a predisposition for osteochondritis dissecans, including: a data storage device containing a first data set representing glucose tolerance test results of an osteochondritis-free horse population; a processor configured to retrieve and compare the first data set with a second data set representing glucose tolerance test results of the subject horse to render a diagnosis of the presence or absence of a predisposition for osteochondritis dissecans in the subject horse; and a user interface operably connected to the processor for communicating to a user the diagnosis.

Implementations of the invention include one or more of the following features. The computer system, includes: an input device connected to interact with the processor to store the second data set on the data storage device; the data storage device is selected from a removable media, a read-only-memory (ROM), a hard drive, or combinations thereof; the data storage device includes a removable media selected from a floppy disk, a magnetic tape, a compact disk, or combinations thereof; the processor performs a statistical comparison of the first and second data sets; the statistical comparison includes a linear regression outlier analysis; the statistical comparison includes determining if the glucose tolerance test results of the subject horse exceed by about one standard deviation or more the mean test results of the osteochondritis dissecans-free horse population; the processor performs a numerical comparison of the first and second data sets to determine if the glucose tolerance test results of the subject horse exceed the numerical range of the glucose tolerance test results of the osteochondritis dissecans-free horse population; and the user interface is selected from a printer, a monitor, a speaker, a modem, a network interface, or combinations thereof.

In general, in one aspect, the invention features a data source for predicting in a subject horse the presence or absence of a predisposition for osteochondritis dissecans, including: a data storage media; and a database retrievably stored on the data storage media, the database representing the glucose tolerance test results of an osteochondritis-free horse population.

Implementations of the invention include one or more of the following features. The data source, includes: the data storage media is selected from a removable media, a readonly-memory (ROM), a hard drive, or combinations thereof; and the data storage media includes a removable media selected from a floppy disk, a magnetic tape, a compact disk, or combinations thereof.

In general, in one aspect, the invention features a method of creating a data source for predicting in a subject horse the presence or absence of a predisposition for osteochondritis dissecans, including: performing a glucose tolerance test on an osteochondritis dissecans-free horse population; creating a first data set representing the results of the glucose tolerance test; and storing the first data set on a data storage device for subsequent comparison to a second data set representing glucose tolerance test results of a subject horse.

Implementations of the invention include one or more of the following features. The method, includes: horses that are less than about sixteen months of age; the glucose tolerance test results include postprandial increases in blood glucose concentrations; the glucose tolerance test results include postprandial increases in blood insulin concentrations; the glucose tolerance test results include postprandial increases in blood glucose concentrations and plasma insulin concentrations; the glucose test results include the rate of postprandial increases in blood glucose concentrations; the glucose tolerance test results include the rate of postprandial increases in blood insulin concentrations; and the glucose tolerance test results include the rate of postprandial increases in blood glucose concentrations and blood insulin concentrations.

In general, in one aspect, the invention features a method for use with a computer of predicting in a horse the presence or absence of a predisposition for osteochondritis dissecans, including: creating a first data set representing the glucose tolerance test results of a subject horse; comparing the first data set to a second data set representing the glucose tolerance test results of an osteochondritis dissecans-free horse population to render a diagnosis regarding a predisposition for osteochondritis dissecans in the subject horse; and reporting the results of the comparison via a user interface of the computer.

Implementations of the invention include one or more of the following features. The method, includes: a statistical comparison of the first and second data sets; the statistical comparison includes determining if the glucose tolerance test results of the subject horse exceed by about two standard deviations or more the mean test results of the osteochondritis dissecans-free horse population; the statistical comparison includes determining if the glucose tolerance test results of the subject horse exceed by about one standard deviation or more the mean test results of the osteochondritis dissecans-free horse population; and the first and second data sets are compared to determine if the glucose tolerance test results of the subject horse exceed the numerical range of the glucose tolerance test results of the osteochondritis dissecans-free horse population.

As used herein, by "osteochondritis dissecans" or "osteochondritis dissecans" is meant a developmental disorder of horses characterized grossly by thickening or loss of articular cartilage and inflammation. osteochondritis dissecans is defined histopathologically by cartilaginous hypertrophy and a failure of capillaries to penetrate cartilage, resulting in a failure of normal mineralization of epiphyseal cartilage. This causes cartilagineous defects at the articular surface and retained cores of cartilage in the metaphyses. Glade, M. J., et al., A dietary etiology for osteochondrotic cartilage; Eq. Vet. Sci. 6:151–155 (1986); Thorp, B. H., et al., Osteochondrosis/dyschondroplasia: a failure of chondrocyte differentiation; Eq. Vet. J. (Suppl.) 16:13–18 (1993); and Fisher, A. T., et al., Osteochondrosis dissecans in the horse; Compendium for Continuing Education 6(3):S123–S128 (1984).

By "osteochondritis dissecans-free horse population" is meant a horse population confirmed by standard diagnostic methods (e.g., radiography, arthroscopy, and/or physical examination) to be free of osteochondrotic lesions and symptoms thereof by the time they reach sixteen months of age. Preferably, the horse population is homogenous for age and is homologous for age with the subject horse to be diagnosed. The horse population preferably is made up of horses less than about sixteen months of age, more preferably of horses less than twelve months of age, and most preferably of horses between two and six months of age. When using horses between two and six months of age, it is preferable to monitor them up to at least sixteen months of age to determine whether they remain free of osteochondritis dissecans. The larger the population of osteochondritis dissecans-free horses, the greater the potential accuracy of the diagnosis of the presence or absence of a predisposition for osteochondritis dissecans in a subject horse. Preferably, the population includes at least about 20 horses. More preferably, the population includes at least about 40 horses. Most preferably, the population includes at least about 60 horses.

By "postprandial" is meant following the administration of a glucose challenge (e.g., oral or nasogastric administration of a glucose source).

By "glucose tolerance test" is meant the administration to a subject horse of a glucose challenge, the collection of urine and/or blood samples at timed intervals following the glucose challenge, and the measurement of urine and/or blood glucose concentrations and/or blood insulin concentrations.

By "glucose tolerance test results" is meant postprandial urine and/or blood glucose concentrations, postprandial blood insulin concentrations, postprandial increases in urine and/or blood glucose concentrations, or postprandial increases in blood insulin concentrations. These results can be used to calculate other results including, but not limited to, the rate of postprandial increases in urine and/or blood glucose concentrations and the rate of postprandial increases in blood insulin concentrations.

By "standardized concentrate" is meant a solid or liquid having a glucose concentration sufficient to cause a maximum increase of about 30–50% in blood glucose concentration and a maximum increase of about 30–50% in plasma insulin concentration following ingestion thereof by osteochondritis dissecans-free horses.

By "glucose concentration analysis system" is meant a system for collecting urine and/or blood samples and determining the concentration of glucose therein.

By "field-administrable glucose challenge" is meant a substance which can be administered in a minimally-invasive manner (e.g., an orally administered solid or liquid feed, a solution administered nasogastrically, or a solution administered intravenously) to a horse. Administration of the field-administrable glucose challenge should produce a maximum increase of about 30–50% in blood glucose concentration and a maximum increase of about 30–50% in plasma insulin concentration in osteochondritis dissecans-free horses within a fixed time period (e.g., 15 minutes for intravenous administration and 1–3 hours for intragastric administration).

By "linear regression outlier analysis" is meant a statistical analysis which identifies a data point which differs significantly (i.e., at a given p value) from the mean of a pool of data points from which the data point has been selected. The difference between the data point and the mean of the pool of data points being statistically significantly greater than that which is consistent with the inherent variability of the variable which the data point represents. The linear regression outlier analysis has been incorporated within the computer data analysis programs (e.g., *Statistixs*, Version 4.1 User Manual, Analytical Software, Tallahassee, Fla. 1994) and described in Weisberg, S., *Applied Linear Regression*; Wiley, New York, N.Y. (1985).

By "p value" or "p<" is meant the probability of observing a sample at least as unlikely as the one observed if the null hypothesis is true. For example, a sample result is statistically significant at the 5% level if, and only if, it leads to a rejection of the null hypothesis when the type I error probability α (i.e., the significance level) is 0.05. Albright, S. C., Hypothesis Testing in *Statistics for Business and Economics*; MacMillan Publishing Company, pg. 416 (1987).

By "electronic glucose analyzer" is meant a glucose analyzer which analyzes the glucose concentration of urine and/or blood samples by converting an analog signal proportional to glucose concentration to a digital signal, and subsequently converting the digital signal into a user readable glucose concentration.

By "diagnostic of" is meant a finding or result which is consistent with, suggestive of, associated with, or symptomatic of an underlying pathology.

By "predisposition" is meant an enhanced likelihood or greater probability of manifesting a particular pathology.

By "blood" is meant whole blood, plasma, and/or serum. Plasma is the fluid portion of whole blood, and is generally separated from whole blood by centrifugation. Plasma clots on standing, therefore, it remains fluid only if an anticoagulant is added. If whole blood is allowed to clot and the clot is removed, the remaining fluid is serum. Serum has essentially the same composition as plasma except that its fibrinogen and clotting factors II, V, and VIII have been removed, and it has a higher serotonin content because of the breakdown of platelets during clotting. Ganong, W. F., Circulating body fluids in *Review of Medical Physiology*; Lange Medical Publications, pg. 419 (1981).

By "insulin analysis" is meant a determination of plasma insulin concentrations by a method previously validated for equine insulin analysis. For example, a radioimmunoassay (RIA) kit is commonly used (Kit TKN1, Diagnostics Products Corp., Los Angeles, Calif.; Freestone, J. F., et al., Exercise induced hormonal and metabolic changes in Thoroughbred horses: effects of conditioning in acepromazine; Equine Vet. J. 23:219–223 (1991). Alternatively, enzyme linked immunosorbent assays (ELISA) or other assays known to those in the art can be used.

Among the advantages of the invention may be one or more of the following. The method and kit of diagnosing a predisposition for osteochondritis dissecans is easily administered, minimally-invasive, inexpensive, and provides diagnostic results within a very short period of time. The method can be performed or the kit utilized in either field or laboratory settings by veterinarians or veterinary technicians. In addition, the kit provides a convenient source of all of the constituents required to diagnose a predisposition for osteochondritis dissecans. The method can be performed in a non-invasive (e.g., urine analysis) or minimally-invasive (e.g., venous blood analysis) manner, thereby eliminating the potential risks associated with more dangerous or invasive methods of diagnosis (e.g., radiography, surgical biopsy). Moreover, the method and kit are considerably less expensive than other presently available means of diagnosing osteochondritis dissecans. Because of these characteristics, the method and kit make it feasible in terms of both time and expense to test all young horses for a predisposition of developing osteochondritis dissecans. Therefore, the deleterious health, financial, and public relations impact of osteochondritis dissecans on horses, horse owners, and horse racing may be significantly reduced.

Other advantages and features will become apparent from the following description.

BRIEF DESCRIPTION OF THE DRAWINGS

FIG. 1 is a flow chart of a method of predicting in a subject horse the presence or absence of a predisposition for osteochondritis dissecans.

DETAILED DESCRIPTION

I. A Method of Predicting in a Horse the Presence or Absence of a Predisposition for Osteochondritis Dissecans Referring to FIG. 1, an embodiment of a method of predicting in a horse the presence or absence of a predisposition for osteochondritis dissecans includes: (1) performing a glucose tolerance test on the subject horse; (2) comparing the glucose tolerance test results of the subject horse to the glucose tolerance test results of an osteochondritis dissecans-free horse population; and (3) diagnosing the subject horse as predisposed to osteochondritis dissecans by numerical comparison or statistical analysis of the glucose tolerance test results.

The glucose tolerance test, whether performed on the subject horse or on the osteochondritis dissecans-free horse population, is a standard glucose tolerance test, and generally includes four steps. In the first step, normal physiologic baseline concentrations of glucose and insulin are established by collecting pre-glucose challenge urine and/or blood samples. Because glucose tolerance test results can be influenced by pre-test diet and activity and test-induced subject agitation, the subject horse is preferably fasted and acclimated to restraint for a fixed period of time (e.g., two to four hours or overnight) prior to obtaining baseline urine and/or blood samples. Test-induced subject agitation also can be reduced by the use of indwelling catheters and/or a urine collection harness for the collection of samples. The indwelling catheters are inserted well in advance of performing the glucose tolerance test (e.g., 12–24 hours). Moreover, the reproducibility of the results and the validity of the comparisons can be enhanced by standardizing the time of testing and the facilities, personnel, and protocols used in performing the glucose tolerance test. Because the handling associated with the testing procedure can also contribute to subject agitation, acclimation of the subject horse to handling prior to the actual collection of data is advisable. Because plasma glucose concentrations following a glucose challenge can be affected by previous ration, it also may be beneficial to standardize the ration fed for several days (e.g., 2–3 days) prior to performing the glucose tolerance test. Jacobs, K. A., et al., Affect of diet on the oral glucose tolerance test in the horse; *J. Vet. Med. Assoc.*

180:884–886 (1992). Since the target population is preferably less than six months of age and usually still nursing, this would mean introduction of grain concentrates into their ration, if not fed grain previously.

In the second step, a glucose challenge or test substance is administered to the subject horse. The glucose challenge can be delivered by a variety of well established methods including oral consumption of a liquid (e.g., glucose "cola") or solid feed, nasogastric administration of a liquid feed or glucose solution, or intravenous administration of a glucose solution. The amount and/or glucose concentration of the test substance will vary depending upon the method of delivery and the body weight of the horse. However, the glucose challenge should be sufficient to produce a maximum increase of about 30–50% increase in urine and/or blood glucose concentrations and a maximum increase of about 30–50% in blood insulin concentration within a fixed period post-administration (e.g., 15 minutes for intravenous administration and 1–3 hours for intragastric administration). Test substances suitable as a glucose challenge in horses include, but are not limited, textured sweet feed (OMOLENE 300™, Purina Mills, St. Louis, Mo.) orally ingested to 0.25% of body weight, a 20% (w/v) glucose solution nasogastrically administered to 0.5 gm glucose/kg of body weight, a 50% (w/v) dextrose solution intravenously administered to 0.5 gm glucose/kg of body weight.

In the third step, urine and/or blood samples are collected from the subject horse at fixed time periods following administration of the glucose challenge. Samples are generally collected at one hour intervals for a total time period of six hours following administration of the glucose challenge. Alternatively, samples can be collected more frequently (e.g., every fifteen minutes) and/or for a shorter period of time post-glucose challenge (e.g., three hours). Urine samples can be collected via a transurethral catheter or as voided samples in a urine collection harness. Blood samples can be collecting from indwelling catheters, or venapuncture.

In the fourth step, the urine and/or blood samples are prepared for analysis via standardized techniques (e.g., centrifugation, drawing off of plasma or urine supernatant), and either analyzed fresh or stored at <0°C. pending analysis. Glucose concentrations of urine and/or blood samples can be determined by a wide variety of standardized laboratory assays. For example, plasma glucose can be determined by an automated hexokinase technique. Gemsaec Centrifugal Analyzer, Electronucteonics, Fairfield, N.J. Portable electronic glucose analyzers are particularly suitable where glucose tolerance tests are performed in a field setting, or when it is desirable to rapidly obtain the glucose tolerance test results. Insulin concentrations can be determined by standardized laboratory methods, typically radioimmunoassay. For example, plasma insulin concentrations can be determined using a radioimmunoassay kit (Kit TKN1, Diagnostics Products Corp., Los Angeles, Calif.), previously validated for equine insulin analysis. Freestone, J. F., et al., Exercise induced hormonal and metabolic changes in Thoroughbred horses: effects of conditioning in acepromazine; Equine Vet. J. 23:219–223 (1991).

Once measured, the glucose and/or insulin concentrations in urine and/or blood samples can be used to calculate standard glucose tolerance test results including, but not limited to, postprandial increases in urine and/or blood glucose concentrations, postprandial increases in blood insulin concentrations, the rate of postprandial increases (i.e., the change in concentration per unit time) in urine and/or blood glucose concentrations, and the rate of postprandial increases in blood insulin concentrations.

One can then numerically compare the glucose tolerance test results of the subject horse to the glucose tolerance test results of an osteochondritis dissecans-free horse population to determine whether the glucose tolerance test results of the subject horse exceed the numerical range of the test results of the osteochondritis dissecans-free horse population. The numerical comparison involves comparing one or more of the above referenced glucose tolerance test results from the subject horse to determine if one or more of the results is outside of the numerical range of the test results of the osteochondritis dissecans-free horse population. Optionally, statistical analysis can be performed to determine if the glucose tolerance test results of the subject horse exceed about two standard deviations or more above the mean test results of the osteochondritis dissecans-free horse population. In another option, statistical analysis can be performed to determine if the glucose tolerance test results of the subject horse exceed about one standard deviation or more above the mean test results of the osteochondritis dissecans-free horse population. These findings are used to support a diagnosis in the subject horse of a predisposition to osteochondritis dissecans.

It will be understood by those of ordinary skill in the art that this method is useful to diagnose a predisposition for the subsequent development of osteochondritis dissecans in a subject horse. It will also be understood that not all subject horses with test results in the various ranges discussed below will always develop osteochondritis dissecans (i.e., there may be false positives). As seen from the data below (see Tables 1 and 2), the test results from normal (NL) and osteochondritis dissecans horse populations have overlapping ranges, with osteochondritis dissecans horses generally having the higher numerical range.

The strength of the diagnosis relates to the test results obtained as follows. In a case in which the test results of a subject horse lies above, that is, exceeds the numerical range of, the test results obtained from horses in an osteochondritis dissecans-free horse population, it is said that the subject horse is very likely to develop osteochondritis dissecans. However, not all subject horses that will develop osteochondritis dissecans will have test results exceeding the numerical range of test results from an osteochondritis dissecans-free horse population.

Therefore, one can perform a statistical analysis to determine if a test result of the subject horse is more than two standard deviations or more above the mean of the test results from an osteochondritis dissecans-free horse population. The test result of the subject horse can be greater than two standard deviations or more above the mean and also be within the absolute numerical range of the results from an osteochondritis dissecans-free population. In this case, it is said that the subject horse is likely to develop osteochondritis dissecans. In a final case, the test result of a subject horse can be more than one standard deviation above the mean of the test results from an osteochondritis dissecans-free horse population and also be within the absolute numerical range of test results for osteochondritis dissecans confirmed horses. The diagnosis of a predisposition for osteochondritis dissecans based on these results is less clear. In this case, a subject horse may develop osteochondritis dissecans. However, the percentage of horses that ultimately develop osteochondritis dissecans will be smaller than those with test results about two standard deviations or more above normal or those exceeding the numerical range of normal (i.e., an increase in the incidence of false positives).

In one embodiment of the method, urine and/or blood glucose concentrations in the subject horse are measured in a field (i.e., non-laboratory) setting, and comparisons are made to glucose tolerance test results of the osteochondritis dissecans-free horse population. In addition, the diagnosis generated by comparing these results can be supported by laboratory measurements of plasma glucose and/or insulin concentrations. Moreover, blood samples can be collected in the field setting and subsequently analyzed for glucose and insulin concentrations in the laboratory.

The comparison of glucose tolerance test results of the subject horse and the osteochondritis dissecans-free horse population can include results derived from glucose concentrations alone (i.e., postprandial increases or rate of postprandial increases in urine and/or blood glucose concentrations), insulin concentrations alone (i.e., postprandial increases or rate of postprandial increases in blood insulin concentration), or a combination of these two measurements. The diagnostic power of these results, from greatest to least, is the combined glucose and insulin concentrations, insulin concentrations alone, and glucose concentrations alone. As noted above, multiple factors (e.g., pretest diet, activity, test-induced subject agitation, etc.) can influence glucose tolerance test results. Because these factors appear to cause greater variation in blood glucose concentrations as compared to blood insulin or urine glucose concentrations, the use of blood insulin concentrations in combination with urine and/or blood glucose concentrations provides for a better correlation between the relative hyperglycemia and/or hyperinsulinemia and a predisposition for osteochondritis dissecans in the subject horse.

When using both glucose and insulin test results, the results are preferably used in parallel. For example, one can compare the glucose concentration results of the subject horse to the results for an osteochondritis dissecans-free horse population. One can also compare the insulin concentration results of the subject horse to the results for an osteochondritis dissecans-free horse population. A diagnosis of a predisposition for osteochondritis dissecans is suggested by test results for both or either test results which lie beyond the numerical range or are more than about two standard deviations or more above the mean or are more than about one standard deviation or more above the mean of test results from an osteochondritis dissecans-free horse population.

The method of diagnosis is preferably performed on horses less than about sixteen months of age (i.e., the age at which horses are no longer considered at risk for developing osteochondritis dissecans). More preferably, horses are evaluated before twelve months of age. Most preferably, horse are evaluated between two and six months of age (i.e., because osteochondritis dissecans lesions can develop as early as four months). Horses can also be evaluated on multiple occasions (e.g., monthly) to support the diagnosis and to follow the development of the disease.

EXAMPLE 1

Hyperglycemia/Hyperinsulinemia After Feeding a Grain to Young Horses with Osteochondritis Dissecans Lesions Plasma glucose and insulin responses to feeding high grain ratios were evaluated in fifteen young Standardbred horses to test the hypothesis that hyperinsulinemia and hyperglycemia may be correlated with osteochondritis dissecans.

Materials and Methods

Data from three two-year-old geldings, four yearling geldings (10–14 months old) and eight weanling colts (3–10 months old) were used. All horses were registered Standardbreds. Four horses (one two-year-old, two yearlings and one weanling) had radiographic evidence of osteochondritis dissecans (osteochondritis dissecans) at the time of testing, the other eleven horses (osteochondritis dissecans-free or normal=NL) had no radiographic abnormalities. The horses were fed 50% textured sweet grain mix (OMOLENE 300™, Purina Mills, St. Louis, Mo., USA) and 50% alfalfa/grass mix hay in amounts that met or exceeded National Research Council (1989) nutrient recommendations for rapid growth. Rations were divided into two equal feedings. Glucose and insulin responses to feeding were measured in 14 horses four times at four week intervals. One NL weanling was only tested twice though on the same protocol as the others. Prior to evaluating postprandial glucose/insulin responses, all horses had been adapted to the ration fed for 4 weeks. The horses were not tested at the same time, however, the same facilities, management, and protocols were used in each experiment with respect to measurement of postprandial glucose and insulin concentrations. The horses were also acclimated to being handled.

Blood for glucose and insulin analyses was drawn from preplaced indwelling venous catheters before feeding grain (1.7 to 2.5 kg, depending on age and body weight) and hay (2 to 3 kg) at 0800 h, then hourly for 6 h. The blood was drawn into heparinized tubes (Vacutainer™, Becton Dickinson, Inc., Rutherford, N.J.), centrifuged immediately, plasma drawn off, and samples stored at <0°C. pending analysis. Plasma glucose concentrations were determined by automated dry chemistry analysis (VetTest 8008 autoanalyzer, IDEXX Inc., Westbrook, Me.). Plasma insulin concentrations were determined by radioimmunoassay (Kit TKN1, Diagnostic Products Corp., Los Angeles, Calif.), previously validated for equine insulin analysis. Freestone, J. F., et al., Exercise induced hormonal and metabolic changes in Thoroughbred horses: effects of conditioning and acepromazine, Equine Vet. J. 23:219–223, (1991).

Rates of change in glucose and insulin concentrations were calculated from the data. Glucose and insulin data were subjected to stepwise regression analysis factoring the effects of trial, presence or absence of osteochondritis dissecans, age and, where appropriate, time after feeding. Statistixs; Version 4.1 User Manual, Analytical Software, Tallahassee, Fla. (1994). For parameters that were identified by regression as contributing significantly ($p<0.05$) to the variability observed, means were compared between groups by two-tailed T-tests. Changes over time were determined by analysis of variance appropriate for repeated measures and Tukeys Test (Analytical Software, 1994).

Results and Discussion

Young horses that had radiographic evidence of osteochondritis dissecans had greater ($p<0.02$) postprandial changes in glucose and insulin when fed high grain rations than did NL horses (n=11) (see Tables 1 and 2). Postprandial plasma glucose and insulin concentrations (mean for all time periods post-administration ± standard deviation) were higher ($p<0.02$) in OCD horses (glucose: 8.59±2.74 mmol/L; insulin: 43.7±32.6 IU/d) than in NL horses (glucose: 7.89±1.38 mmol/L; insulin: 27.8±17.8 IU/d). The mean rate of glucose increase was higher in OCD horses than NL horses at 1 hour after feeding (NL: 0.03±0.021 mmol/min; OCD: 0.068±0.037 mmol/min; $p<0.01$) and 2 hours (NL: 0.005±0.016 mmol/min; OCD: 0.018±0.028 mmol/min; $p<0.01$). Concomitant insulin rates of increase also differed between groups at one hour (NL: 0.42±0.24 IU/min; OCD: 0.64±0.23 IU/min; $p<0.001$) and at two hours after feeding (NL: 0.03±0.16 IU/min; OCD: 0.29±0.35 IU/min; $p<0.01$). These results indicate that young horses with OCD lesions have greater postprandial hyperglycemia and hyperinsulinemia when fed high grain ratios than those that do not have lesions.

TABLE 1

PLASMA GLUCOSE (mmol/L) IN NORMAL (NL) VERSUS OCD HORSES AFTER FEEDING MEALS OF SWEET GRAIN MIX PLUS HAY

| Group | Time after feeding (hours) | | | | | | | SEM[3] |
|---|---|---|---|---|---|---|---|---|
| | 0 | 1 | 2 | 3 | 4 | 5 | 6 | |
| NL[1] | 6.89[a] ±0.90 | 9.12[a] ±1.33 | 8.85[d,e] ±1.73 | 8.29[c,d] ±1.19 | 7.78[b,c] ±0.82 | 7.29[a,b] ±0.75 | 7.01[a] ±0.76 | .17 |
| OCD[2] | 6.22[a]* ±0.67 | 10.33[c,d]** ±2.08 | 11.4[d]** ±2.69 | 10.18[c,d]* ±2.75 | 8.59[b,c] ±2.0 | 7.01[a,b] ±1.4 | 6.36[a]* ±1.08 | .49 |

[1]Values are means (±SD) for 4 replicates for 10 horses and 2 replicates for one horse.
[2]Values are means (±SD) for 4 replicates for four horses.
[3]SEM = Standard error of mean.
[a,b,c,d,e]Means with different superscripts differ within group (p < 0.05).
*OCD differs from NL within time period (p < 0.05).
**OCD differs from NL within time period (p < 0.01).

TABLE 2

PLASMA INSULIN (IU/dl) IN NORMAL (NL) VERSUS OCD HORSES AFTER FEEDING MEALS OF SWEET GRAIN MIX PLUS HAY

| Group | Time after feeding (hours) | | | | | | | SEM[3] |
|---|---|---|---|---|---|---|---|---|
| | 0 | 1 | 2 | 3 | 4 | 5 | 6 | |
| NL[1] | 10.2[a] ±5.3 | 35.8[c] ±15.1 | 37.4[c] ±17.6 | 36.9[c] ±20.0 | 34.2[c,d] ±20.0 | 25.4[b,c] ±12.1 | 18.9[a,b] ±9.0 | 2.3 |
| OCD[2] | 8.8[a] ±6.7 | 48.1[b,c]** ±12.4 | 65.5[c]** ±26.9 | 66.1[c]** ±36.1 | 61.7[b,c]* ±40.1 | 35.1[a,b] ±21.8 | 20.5[a] ±14.5 | 6.3 |

[1]Values are means (±SD) for 4 replicates for 10 horses and 2 replicates for one horse.
[2]Values are means (±SD) for 4 replicates for 4 horses.
[3]SEM = Standard error of mean.
[a,b,c,d]Means with different superscripts differ (p < 0.05) within group.
*OCD differs from NL within time period (p < 0.05) by Two way T-Test.
**OCD differs from NL within time period (p < 0.01) by Two way T-test.

Within the NL population, weanling colts and yearling geldings (i.e., 3–14 months of age) (n=9) had greater (p<0.001) postprandial increases in glucose than did two year old horses, suggesting a relative glucose intolerance in the older horses (n=2) (see Table 3). However, insulin responses did not differ between the age groups (p>0.50) (see Table 4). As a result, the calculated glucose/insulin ratio was lower in two year olds than in the younger colts (2 year old: 0.33±0.25, 3 to 14 months: 0.42±0.28; p<0.01), suggesting relative insulin resistance in the younger animals. The existence of glucose intolerance and apparent insulin resistance in horses <14 months old as compared to horses >16 months old indicates that hyperglycemia and/or hyperinsulinemia is correlated with the development of osteochondritis dissecans in young horses.

TABLE 3

PLASMA GLUCOSE (mmol/L) in NORMAL (NL) COLTS 3 TO 14 MONTHS OLD AND GELDINGS VERSUS NL TWO-YEAR-OLD GELDINGS AFTER FEEDING MEALS OF SWEET GRAIN MIX PLUS HAY

| NL AGE | Time after feeding (hours) | | | | | | | SEM[3] |
|---|---|---|---|---|---|---|---|---|
| | 0 | 1 | 2 | 3 | 4 | 5 | 6 | |
| 3–14[1] month olds | 7.17[a] ±0.67 | 9.50[d] ±1.14 | 9.36[d] ±1.53 | 8.56[c] ±1.14 | 8.00[b,c] ±0.75 | 7.49[a,b] ±0.68 | 7.27[a] ±0.64 | .17 |

TABLE 3-continued

PLASMA GLUCOSE (mmol/L) in NORMAL (NL) COLTS 3 TO 14 MONTHS OLD
AND GELDINGS VERSUS NL TWO-YEAR-OLD
GELDINGS AFTER FEEDING MEALS OF SWEET
GRAIN MIX PLUS HAY

| NL AGE | Time after feeding (hours) | | | | | | | SEM[3] |
|---|---|---|---|---|---|---|---|---|
| | 0 | 1 | 2 | 3 | 4 | 5 | 6 | |
| Two-[2] year-olds | 5.72[a]* ±0.91 | 7.53[d]** ±0.85 | 6.71[a,b,c]** ±0.65 | 7.14[c,d]** ±0.59 | 6.86[b,c,d]** ±0.43 | 6.45[a,b,c]** ±0.46 | 6.06[a,b]** ±0.84 | .23 (.16) |

[1]Values are means (±SD) for 4 replicates for 9 horses.
[2]Values are means (±SD) for 4 replicates for 2 horses.
[3]SEM = Standard error of mean.
[a,b,c,d,e]Means with different superscripts differ (p < 0.05) within group.
*NL 3–14 month olds differ from NL Two year olds within time period (p < 0.05) by Two way T-test.
**NL 3–14 month olds differ from NL Two year olds within time period (P < 0.01) by Two way T-test.

TABLE 4

PLASMA INSULIN (IU/dl) IN NORMAL (NL) COLTS 3 TO 14 MONTHS
OLD COLTS AND GELDINGS VERSUS NL TWO-YEAR-OLD GELDINGS
AFTER MEALS OF SWEET GRAIN MIX PLUS HAY

| NL AGE | Time after feeding (hours) | | | | | | | SEM[3] |
|---|---|---|---|---|---|---|---|---|
| | 0 | 1 | 2 | 3 | 4 | 5 | 6 | |
| 3–14[1] month old | 9.99[a] ±4.41 | 33.3[c,d] ±12.8 | 36.9[d] ±17.74 | 35.7[c,d] ±20.53 | 34.3[c,d] ±21.18 | 25.1[b,c] ±13.18 | 19.4 ±9.85 | 2.6 |
| Two-[2] year-olds | 11.5[a] ±8.5 | 46.4[c] ±19.96 | 39.6[c] ±17.85 | 41.9[b,c] ±17.65 | 34.0[a,b,c] ±14.98 | 26.5[a,b] ±5.94 | 16.6[a,b] ±3.57 | 4.9 |

[1]Values are means (±SD) for 4 replicates for 9 horses.
[2]Values are means (±SD) for 4 replicates for 2 horses.
[3]SEM = Standard error of mean.
[a,b,c,d,]Means with different superscripts differ within group (p < 0.05).
*NL 3–14 month olds differ from NL Two year olds within time period (p < 0.05) by Two way T-test.
**NL 3–14 month olds differ from NL Two year olds within time period (P < 0.01) by Two way T-test.

Plasma glucose concentrations following a glucose or meal challenge may be affected by previous ration, excitement, rate of gastric emptying, glucose absorption rates and relative insulin sensitivity. Jacobs, K. A., et al., Effect of diet on the oral glucose tolerance test in the horse, J. Am. Vet. Med. Assoc. 180:884–886 (1992); Argenzio, R. A., et al., Effect of diet on glucose entry and oxidation rates in ponies, J. Nutr. 102:879–892 (1972). The differences reported here were not due to differences in rations fed. Though not all of the colts and geldings were tested at the same time, all were fed the same hay:grain ratio and baseline grain in all tests. Adaptation to the rations were the same for all tests. The same facilities, management, and protocols were used in each experiment with respect to measurement of postprandial glucose and insulin. Excitement also was not a factor in glucose/insulin responses. The colts were accustomed to being handled, regardless of age, and samples were drawn from indwelling catheters that had been preplaced 18 to 20 hours prior to the test to preclude excitement associated with repeated vein puncture. Whether the postprandial hyperinsulinemia and hyperglycemia were due to insulin resistance or differences in glucose digestion/absorption rates were not determined in these trials.

Conclusions

Young horses with osteochondritis dissecans lesions have greater postprandial hyperglycemia and hyperinsulinemia when fed high grain rations than those that do not have lesions. The existence of glucose intolerance and apparent insulin resistance in horses <14 months old relative to two year old horses supports the finding that hyperglycemia and/or hyperinsulinemia is correlated with the development of osteochondritis dissecans in young horses. Early osteochondritis dissecans (at <6 month of age) lesions have a relatively high heritability. Foals which develop these lesions can be identified at an early age by their relative glucose intolerance as compared to non-predisposed foals.

II. A Method of Screening a Population of Horses for the Presence or Absence of a Predisposition Toward Developing Osteochondritis Dissecans Referring to FIG. 2, the method of screening a population of horses for the presence or absence of a predisposition toward developing osteochondritis dissecans includes: (1) performing a glucose tolerance test on a population of horses; (2) calculating the results of the glucose tolerance test for the horse population; and (3) diagnosing in horses the presence or absence of a predisposition toward developing osteochondritis dissecans by statistical analysis of the glucose tolerance test results.

Figure 2:
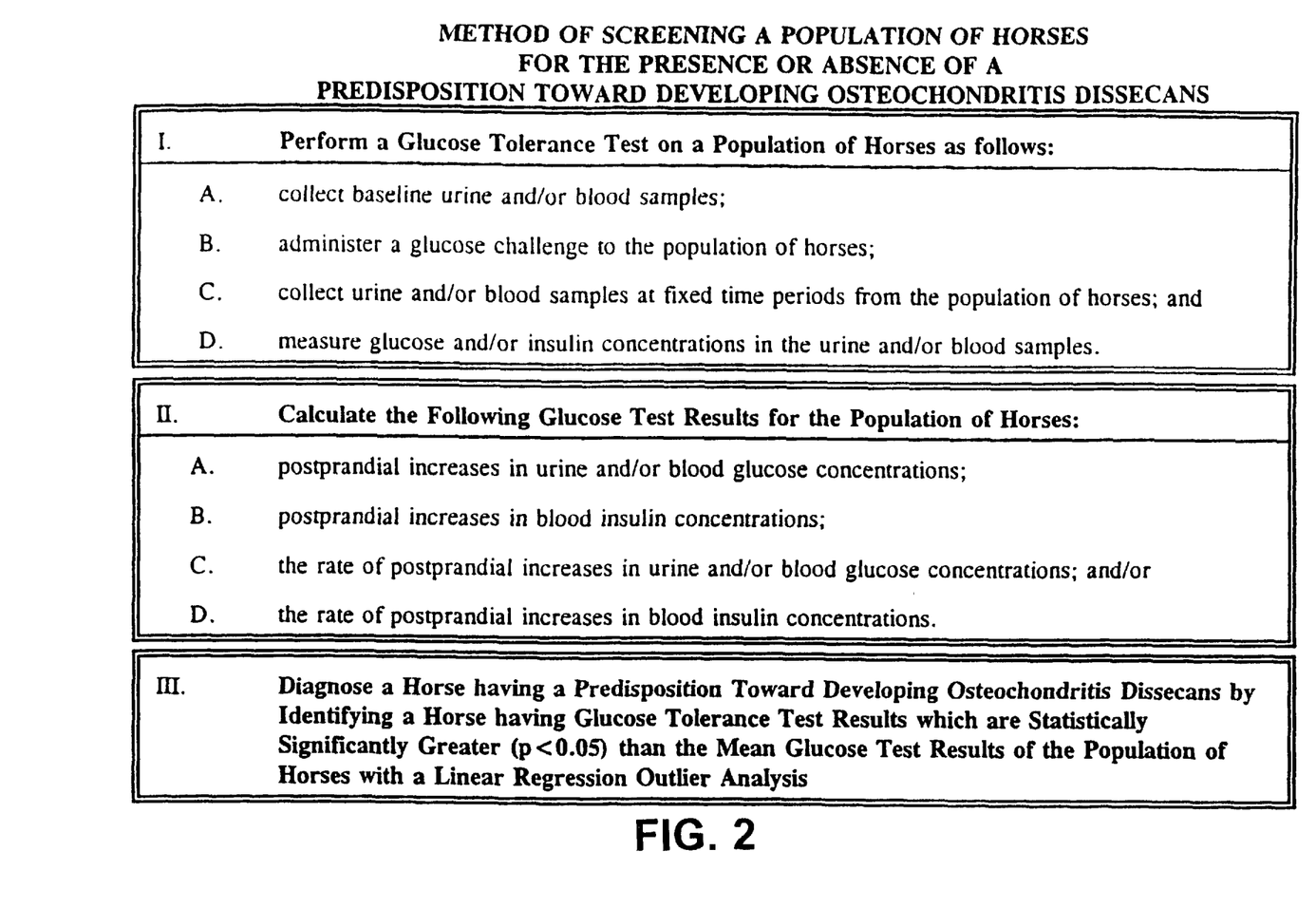
FIG. 2 is a flow chart of a method of screening a population of horses for the presence or absence of a predisposition toward developing osteochondritis dissecans.

The glucose tolerance test is performed on the horse population to be screened essentially as described above. Of course, the larger the population of horses screened, the greater the potential accuracy of the diagnosis. Preferably, the population includes at least about 20 horses. More preferably, the population includes at least about 40 horses. Most preferably, the population includes at least about 60 horses.

The glucose tolerance test results for the population of horses are calculated as described above. The test results are then analyzed statistically to identify horses having glucose tolerance test results which are significantly greater than the mean glucose test results of the entire population of horses. For example, a linear regression outlier analysis can be performed on the glucose tolerance test results for the entire population. Those horses having one or more glucose tolerance test results which are statistically significantly greater than the mean values for the population (i.e., the test results is an outlier) are diagnosed as having a predisposition toward developing osteochondritis dissecans. Although the confidence level for the statistical analysis can be as low as $p<0.001$, typically, a $p<0.05$ is used.

III. Kits for Predicting in a Horse the Presence or Absence of a Predisposition for Osteochondritis Dissecans A. A Kit for Field Prediction The kit for predicting in a horse the presence or absence of a predisposition for osteochondritis dissecans includes a field-administrable glucose challenge, a glucose concentration analysis system, and a data source containing glucose tolerance test results for an osteochondritis dissecans-free horse population. The field-administrable glucose challenge can be any test substance which is administrable in a minimally-invasive manner. Although nasogastric and intravenous solutions can be used, typically, an orally administered solid or liquid feed is preferred. Standardized concentrates such as "colas" (e.g., high glucose concentration solutions) or textured sweet grain mixes (e.g., Omolene 300™, Purina Mills, St. Louis, Mo.) combine the advantage of being easily administered (i.e., highly palatable to the subject horse) and easily packaged and transported (i.e., because of their relatively small weight and volume).

The glucose concentration analysis system includes apparatus for collecting the urine and/or blood samples and determining the glucose concentration therein. For example, the apparatus for collecting urine and/or blood samples and for determining glucose concentration can be a commercially available glucose indicator strip (e.g., calorimetric glucose indicator strips). Where blood glucose concentration is to be determined, the glucose concentration analysis system also includes an alcohol wipe or other means for prepping the collection site and a needle and a syringe, or other device for obtaining blood from the subject horse.

The glucose concentration in urine and/or blood samples can also be determined with any one of a number of widely available electronic glucose analyzers. The electronic glucose analyzer can simply provide the glucose concentration of the sample or, alternatively, can include a data source containing glucose tolerance test results for an osteochondritis dissecans-free horse population. The electronic glucose analyzer can be configured to provide the operator (e.g., the veterinarian or veterinarian technician) with a variety of results and/or comparisons of the glucose tolerance test. For example, the electronic glucose analyzer can provide the operator with the urine and/or blood glucose concentrations of the subject horse and the mean and/or numerical range of glucose concentrations from the osteochondritis dissecans-free horse population. Alternatively, the electronic glucose analyzer can calculate the postprandial increases and rates of postprandial increase in urine and/or blood glucose concentrations of the subject horse, and can report and/or compare these results to those of the osteochondritis dissecans-free horse population. Moreover, the electronic blood glucose analyzer can be preprogrammed to render a diagnosis of a predisposition for osteochondritis dissecans based on the comparisons described herein.

The data source containing the glucose tolerance test results for the osteochondritis dissecans-free horse population can be presented in a wide variety of formats. For example, in the simplest case, the data source can include a table, chart, graph, or equation representing these data for visual or numerical comparison with the test results of the subject horse. Alternatively, the data source can include a calorimetric chart depicting by color gradation the mean ± standard deviations and/or numerical range of urine and/or blood glucose concentrations in the osteochondritis dissecans-free horse population. As described previously, the data source also can be stored in the electronic glucose analyzer in digital form.

Where the kit is used for prescreening, or a determination of blood insulin concentrations is desired, the kit can further include a venous blood collection and containment system. For example, the venous blood collection and containment system can include a needle and a syringe. Alternatively, blood can be collected in evacuated tubes, with or without anticoagulant coatings (e.g., Vacutainer™, Becton Dickinson, Inc., Rutherford, N.J.).

B. A Kit for Field Collection and Laboratory Prediction

The field collection and laboratory prediction kit for predicting in a horse the presence or absence of a predisposition for osteochondritis dissecans includes a field-administrable glucose challenge, a venous blood collection and containment system, instructions for performing a field glucose tolerance test, and a data source containing the glucose tolerance results of an osteochondritis dissecans-free horse population.

The field-administrable glucose challenge, the venous blood collection and containment system, and the data source are as described above. The instructions for performing the field glucose tolerance test are essentially those described for the method depicted in FIG. 1. The principle difference being that only blood samples are collected, which subsequently are measured in a laboratory versus a non-laboratory setting.

Because the diagnosis provided by this kit can be based upon comparison of blood glucose and/or insulin concentrations in the subject horse and the osteochondritis dissecans-free horse population, use of this kit is indicated where enhanced accuracy is valued over the rapidity with which results are obtained. Use of this kit also may be indicated where the number of samples to be collected exceeds that which can be efficiently and conveniently handled by the operator.

IV. A Data Source for Predicting in a Subject Horse the Presence or Absence of a Predisposition for Osteochondritis Dissecans The method of creating a data source for predicting in a subject horse the presence or absence of a predisposition for osteochondritis dissecans includes performing a glucose tolerance test on an osteochondritis dissecans-free horse population, creating a data set representing the results of this glucose tolerance test, and storing the data on a data storage device for subsequent comparison to the glucose tolerance test results of a subject horse.

The glucose tolerance test is performed essentially as described above. A data set is created from the results of the glucose tolerance test and is selected from, but is not limited to, postprandial increases in urine and/or blood glucose concentrations, postprandial increases in blood insulin concentrations, the rate of postprandial increases in urine and/or blood glucose concentrations, and/or the rate of postprandial increases in blood insulin concentrations. The data set can be stored on a data storage device in either analog or digital form. For example, data in an analog form can be stored on reference cards which depict the data in tabular, graphic or numerical equation form. Analog data can also be stored in the form of a color chart to be used in correspondence with calorimetric glucose indicator strips as described above. Where the data is in digital form, it can be stored on a removable media, a read-only-memory (ROM), a hard drive, or combinations thereof. Other digital storage media will be apparent to those skilled in the electronic arts. When stored in digital form, the data can be accessed by an electronic blood glucose analyzer, a laboratory instrument used to calculate and analyze glucose tolerance test results (i.e., glucose and/or insulin concentrations), or a computer system. The data in digital form can also be rendered portable by storing on a removable media such as floppy disk, a magnetic tape, a compact disk, or combinations thereof. Data in this form is particularly suitable for use in a computer program or a computer system.

A computer program can be created to perform a series of steps resulting in the output of a diagnosis regarding the presence or absence of a predisposition of osteochondritis dissecans in a subject horse. In the first step of the computer program, a first data set is created which represents the glucose tolerance test results of the subject horse. In the second step of the computer program, the first data set is compared to a second data set which represents the glucose tolerance test results of an osteochondritis dissecans-free horse population. This comparison is undertaken to render a diagnosis regarding a predisposition for osteochondritis dissecans in the subject horse. In the third step of the computer program, the results of the comparison are reported to a user via a user interface.

Creation of the first data set can be accomplished by user input of either the raw data from the glucose tolerance test (e.g., urine and/or blood glucose or blood insulin concentrations at a given time point) or the results calculated therefrom (e.g., postprandial increases of glucose and/or insulin concentrations). Alternatively, the first data set can be created from the raw data or calculated results provided by a field or a laboratory instrument which measures urine and/or blood glucose and/or insulin concentrations.

The comparison of the first data and second data sets can include a determination of whether the glucose tolerance test results of the subject horse exceed the numerical range of the test results of the osteochondritis dissecans-free horse population. Optionally, statistical analysis can be performed to determine if the glucose tolerance test results of the subject horse exceed about two standard deviations or more above the mean test results of the osteochondritis dissecans-free horse population. In another option, statistical analysis can be performed to determine if the glucose tolerance test results of the subject horse exceed about one standard deviation or more above the mean test results of the osteochondritis dissecans-free horse population. As detailed above, the comparison of glucose tolerance test results of the subject horse and the osteochondritis dissecans-free horse population can include glucose concentrations alone, insulin concentrations alone, or both of these measurements.

Figure 3:
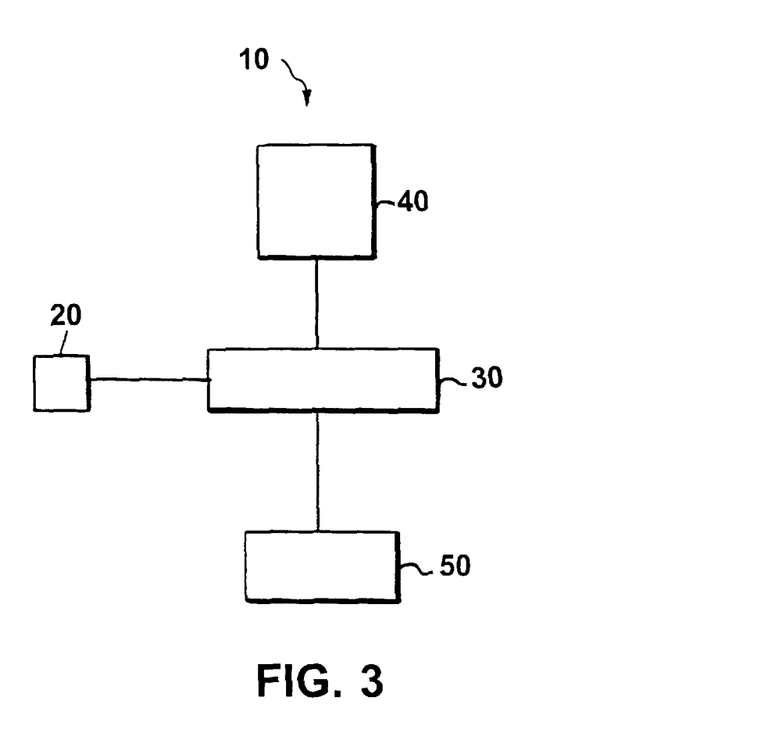
FIG. 3 is a schematic of a computer system for predicting in a horse the presence or absence of a predisposition for osteochondritis dissecans.

Referring to FIG. 3, a computer system 10 for predicting in a subject horse the presence or absence of a predisposition for osteochondritis dissecans includes a data storage device 20 (e.g., a removable media, a read-only-memory (ROM), a hard drive, and combinations thereof) containing a first data set which represents the glucose tolerance test results of an osteochondritis-free horse population. A processor 30 (e.g., a central processing unit, an add-in card, or combinations thereof) is configured to retrieve and compare the first data set with a second data set representing the glucose tolerance test results of a subject horse. The processor compares the data sets by numerical comparison or statistical analysis as described above to render a diagnosis regarding a predisposition for osteochondritis dissecans in the subject horse. Once the comparison has been completed, the processor communicates the diagnosis to a user via the user interface 40 (e.g., a computer monitor, a liquid crystal display, a speaker, a printer, a modem, a network interface or combinations thereof). The data set representing the glucose tolerance test results of the subject horse can be input into the computer directly from the device which measures urine and/or blood glucose or insulin concentrations. Alternatively, the data set representing glucose tolerance test results of the subject horse can be input by a user into the computer system via input device 50 (e.g., a keyboard, a numerical pad, a touch screen, a microphone, a pointing device, or combinations thereof).

Other embodiments are within the scope of the following claims.

What is claimed is:

1. A method of predicting in a subject horse the presence or absence of a predisposition for osteochondritis dissecans, comprising:

performing a glucose tolerance test on the subject horse; and comparing the glucose tolerance test results of the subject horse and the glucose tolerance test results of an osteochondritis dissecans-free horse population, wherein glucose tolerance test results of the subject horse exceeding the numerical range of the glucose tolerance test results of the osteochondritis dissecans-free horse population are diagnostic of a predisposition for osteochondritis dissecans in the subject horse.

2. The method of claim 1, wherein the subject horse and horses in the osteochondritis dissecans-free horse population are less than about sixteen months of age.

3. The method of claim 1, wherein the glucose tolerance test results include postprandial increases in blood glucose concentrations.

4. The method of claim 1, wherein the glucose tolerance test results include postprandial increases in blood insulin concentrations.

5. The method of claim 1, wherein the glucose tolerance test results include postprandial increases in blood glucose concentrations and blood insulin concentrations.

6. The method of claim 1, wherein the glucose test results include the rate of postprandial increases in blood glucose concentrations.

7. The method of claim 1, wherein the glucose tolerance test results include the rate of postprandial increases in blood insulin concentrations.

8. The method of claim 1, wherein the glucose tolerance test results include the rate of postprandial increases in blood glucose concentrations and blood insulin concentrations.

9. A method of predicting in a subject horse the presence or absence of a predisposition for osteochondritis dissecans, comprising:

performing a glucose tolerance test on the subject horse; and comparing the glucose tolerance test results of the subject horse against the glucose tolerance test results of an osteochondritis dissecans-free horse population, wherein glucose tolerance test results of the subject horse exceeding about two standard deviations or more above the mean glucose tolerance test results of the osteochondritis dissecans-free horse population are diagnostic of a predisposition for osteochondritis dissecans in the subject horse.

10. A method of screening a population of horses for the presence or absence of a predisposition toward developing osteochondritis dissecans, comprising:

performing a glucose tolerance test on the population of horses; and identifying horses having glucose tolerance test results which are statistically significantly greater ($p<0.05$)

than the mean glucose tolerance test results of the population by a linear regression outlier analysis, wherein the horses so identified are diagnosed as having a predisposition toward developing osteochondritis dissecans.

11. A kit for predicting in a subject horse the presence or absence of a predisposition for osteochondritis dissecans, comprising:

a field-administrable glucose challenge;

a glucose concentration analysis system; and a data source containing glucose tolerance test results for an osteochondritis dissecans-free horse population.

12. The kit of claim 11, wherein the glucose challenge includes a standardized concentrate for oral administration.

13. The kit of claim 11, wherein the glucose concentration analysis system includes a calorimetric glucose indicator strip.

14. The kit of claim 13, wherein the calorimetric glucose indicator strip includes a blood glucose indicator strip.

15. The kit of claim 11, wherein the glucose concentration analysis system includes an electronic glucose analyzer.

16. The kit of claim 15, wherein the electronic glucose analyzer includes an electronic blood glucose analyzer.

17. The kit of claim 15, wherein the data source is stored in the electronic glucose analyzer.

18. The kit of claim 17, wherein the electronic glucose analyzer compares the postprandial increase in glucose concentration of a subject horse to the glucose tolerance test results of the osteochondritis dissecans-free horse population to render a diagnosis of a predisposition for osteochondritis dissecans.

19. The kit of claim 11, further comprising a venous blood collection and containment system for laboratory analysis of blood glucose and insulin concentrations.

20. A kit for predicting in a subject horse the presence or absence of a predisposition for osteochondritis dissecans, comprising:

a field-administrable glucose challenge;

a venous blood collection and containment system;

instructions for performing a field glucose tolerance test; and a data source containing glucose tolerance test results of an osteochondritis dissecans-free horse population for comparison to glucose tolerance test results in a subject horse and diagnosing the presence of absence of a predisposition for osteochondritis dissecans in the subject horse.

* * * * *